US006480148B1

(12) United States Patent
Wilson et al.

(10) Patent No.: US 6,480,148 B1
(45) Date of Patent: *Nov. 12, 2002

(54) METHOD AND APPARATUS FOR NAVIGATION GUIDANCE

(75) Inventors: Raymond P Wilson, Christchurch (NZ); Harold L. Longaker, Houston, TX (US)

(73) Assignee: Trimble Navigation Ltd., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/653,740

(22) Filed: Sep. 1, 2000

Related U.S. Application Data

(63) Continuation of application No. 09/252,897, filed on Feb. 18, 1999, now Pat. No. 6,140,957, which is a continuation-in-part of application No. 09/041,857, filed on Mar. 12, 1998, now Pat. No. 6,052,083.

(51) Int. Cl.⁷ .............................. H04B 7/185; G01S 5/02
(52) U.S. Cl. ............................ 342/357.08; 342/357.17; 342/419; 701/213
(58) Field of Search ...................... 342/357.08, 357.17, 342/419, 357.06; 701/213

(56) References Cited

U.S. PATENT DOCUMENTS

| | | |
|---|---|---|
| 3,885,095 A | 5/1975 | Wolfson et al. |
| 4,350,969 A | 9/1982 | Greer |
| 5,159,760 A | 11/1992 | Spiegel et al. |
| 5,379,045 A | 1/1995 | Gilbert et al. |
| 5,497,271 A | 3/1996 | Mulvanny et al. |
| 5,504,482 A | 4/1996 | Schreder |
| 5,519,620 A | 5/1996 | Talbot et al. |
| 5,552,993 A | 9/1996 | Buchwitz et al. |
| 5,568,152 A | 10/1996 | Janky et al. |
| 5,635,907 A | 6/1997 | Bernard et al. |
| 5,644,318 A | 7/1997 | Janky et al. |
| 5,672,820 A | 9/1997 | Rossi et al. |
| 5,751,576 A | 5/1998 | Monson |
| 5,903,235 A * | 5/1999 | Nichols ....................... 342/357 |
| 6,140,957 A * | 10/2000 | Wilson et al. ......... 342/357.08 |

OTHER PUBLICATIONS

Tom Logsdon, Understanding the NAVSTAR GPS, GIS, and IVHS, "*Integrated Navigation Systems*", pp. 110–122.

* cited by examiner

*Primary Examiner*—Dao Phan
(74) *Attorney, Agent, or Firm*—Blakely Sokoloff Taylor & Zafman LLP

(57) ABSTRACT

A position identification system, that employs satellite navigational or similar positioning technology is provided. In one embodiment, the position identification system includes a receiver for receiving position signals from a positioning system; an orientation device that is configured to rotate about at least one axis; a pointing element coupled to the orientation device to provide indication of a direction to a desired position; and a processor that is coupled to the receiver to receive the position signals. The processor computes a current position of the position identification system based upon the position signals. The processor directs the orientation device, based upon the current position and the desired position, with the pointing device tracking the direction to the desired position as the current position changes. Using the positioning system, a pointing device is used to identify the direction to the desired location to the user of the positioning system. The positioning system receives a first position corresponding to the desired location. A second position is determined corresponding to the device's current location. Then the pointing element is oriented such that the pointing element is substantially aligned with the first position indicating the direction to the desired. The position signals are updated so that, if the device's current position changes, the pointing device will track the direction to the desired position.

5 Claims, 11 Drawing Sheets

METHOD AND APPARATUS FOR NAVIGATION GUIDANCE

This patent application is a continuation of and claims priority to Ser. No. 09/252,897 filed Feb. 18, 1999, now U.S. Pat. No. 6,140,957, issued Oct. 31, 2000, entitled METHOD AND APPARATUS FOR NAVIGATION GUIDANCE which is a continuation-in-part of and claims priority to Ser. No. 09/041,857 filed Mar. 12, 1998, now U.S. Pat. No. 6,052,083,issued Apr. 18, 2000, entitled METHOD AND APPARATUS FOR POSITIONING IDENTIFICATION.

FIELD OF THE INVENTION

The present invention relates to navigating to a predetermined position using positioning information from satellite navigational equipment or similar positioning technology.

BACKGROUND OF THE INVENTION

The art of surveying and mapping has dramatically changed through the use of satellite navigation equipment. Satellite survey devices include receivers that receive position signals from the global positioning system (GPS), Global Navigation Satellite System (GLONASS) receiver or other satellite or pseudolite systems. The position signals are used to compute the position of the receiver.

While selective availability (S/A) and environmental conditions may degrade the position signals to 100 meter accuracy, differential correction (DGPS) and real time kinematic (RTK) processes may be employed increase accuracy to the within 1 to 2 centimeter accuracy. RTK and real time computation of DGPS both require the use of an additional radio frequency receiver for reception of additional data that is used to compute a corrected, more accurate, position. Thus, the satellite survey device which is typically called the "rover device", includes a range pole for identifying the point for which a location is to be computed, a user input/output device for entry and display of information and data, a satellite receiver and a radio receiver.

The range pole has attached to it an antenna for receiving GPS signals and a circular level or vial. The user holds the range pole and moves the range pole about until the level indicates that the range pole is vertically oriented and the bottom of the pole touches a location to be surveyed. Once vertically oriented, the information received via the GPS antenna can be used to accurately compute the position of the location. Typically, the user will have a backpack that includes a wireless link, such as a radio modem, for receiving additional data, e.g., correction signals, from a reference station, e.g., a differential GPS (DGPS) base station. Using DGPS technology, more precise measurements are obtained. The backpack also contains equipment and circuits for generating positional information based upon the signals received through the antenna and the wireless link. The data collection device enables the user to make manual entries, and also provides a visual reading of the survey measurements obtained.

A typical method of navigating to a known position will now be described. The user navigates to a location of interest by inputting the desired position in latitude and longitude (or any convenient x, y, z coordinate system) to the survey device and then following on screen directions such as an indication of the direction and distance from the user's current position. The on screen indications are useful while the user is approaching the location of interest from a distance; however, the on screen indication may change wildly when the user is very close to the desired position. Therefore, once the user is within a few meters, the user's pace must be slowed to assure the point is not passed over. When the user has identified an estimated location that is believed to be the location of interest, the process of confirming the estimated location may begin. This iterative process typically involves placing the range pole over the estimated location, leveling the range pole, receiving a measurement, and adjusting the placement of the range pole. This confirmation process continues until the measurement received matches the position of the location of interest. After receiving feedback from the input/output device the user adjusted the placement of the range pole to another location. Upon receiving the second measurement, the user adjusted the placement of the range pole to yet another location. At this point, the user received confirmation that the range pole was in fact positioned over the desired location.

Land seismic surveys are commonly performed using vibroseis trucks with these trucks providing the seismic energy. The trucks vibrate at predetermine points that are usually marked with stakes that have been placed by surveyors. During operations, the vibroseis trucks navigate from point to point using these survey stakes. One problem with using survey stakes is that they can be destroyed or removed by things such as cattle, vehicles, and vandals. Another problem is the cost associated with the survey stake out. In addition, the vibroseis trucks used in these operations are very large and make frequent short moves while in formation with other trucks. Due to these and other problems, some vibroseis trucks have on board navigation systems. However, if drivers of these trucks have to divert their attention from the safe steering of the trucks to read a navigation display console, unsafe conditions resulting in accidents may occur.

SUMMARY OF THE INVENTION

The present invention describes a surveying device, referred to as a position identification system, that employs satellite navigational or similar positioning technology. In one embodiment, the position identification system includes a receiver for receiving position signals from a positioning system; an orientation device that is configured to rotate about at least one axis; a pointing element coupled to the orientation device to provide indication of a direction to a desired position; and a processor that is coupled to the receiver to receive the position signals. The processor computes a current position of the position identification system based upon the position signals. The processor directs the orientation device, based upon the current position and the desired position, with the pointing device tracking the direction to the desired position as the current position changes.

Using the positioning system, a pointing device is used to identify the direction to the desired location to the user of the positioning system. The positioning system receives a first position corresponding to the desired location. A second position is determined corresponding to the device's current location. Then the pointing element is oriented such that the pointing element is substantially aligned with the first position indicating the direction to the desired. The position signals are updated so that, if the device's current position changes, the pointing device tracks the direction to the desired position.

BRIEF DESCRIPTION OF THE DRAWINGS

The features and advantages of the present invention will be apparent to one skilled in the art from the following detailed description in which:

FIG. 6A and FIG. 6B illustrate views of the handheld surveying device according to one embodiment of the present invention.

DETAILED DESCRIPTION

In the following description, for purposes of explanation, numerous details are set forth in order to provide a thorough understanding of the present invention. However, it will be apparent to one skilled in the art that these specific details are not required in order to practice the present invention. In other instances, well known electrical structures and circuits are shown in block diagram form.

Figure 1:
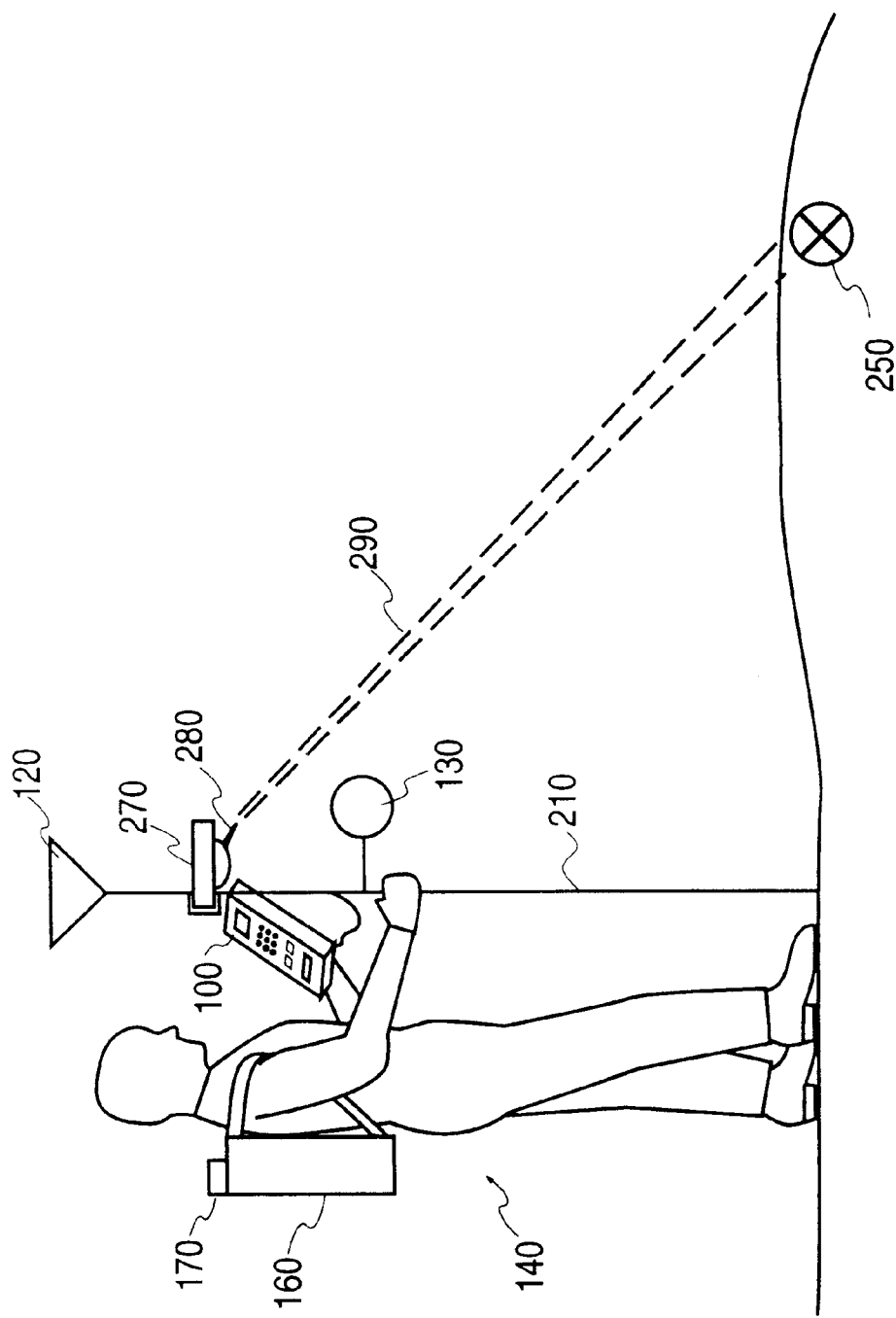
FIG. 1 is a simplified drawing of a survey device according to one embodiment of the present invention.

The surveying device of the present invention provides an improved method of identifying a known location of interest by eliminating the iterative and time consuming confirmation process described above. A simplified illustration of an exemplary surveying device is shown in FIG. 1. As discussed further below, when the user 140 is within a predetermined distance of the desired position, the device may be used to identify the location of the position by illuminating the point 250 on the ground using a small, eye-safe, visible, fine beam laser or similar pointing device. Using the device, the user 140 can identify the location 250 of a particular position. In this manner, the device eliminates the need for the location estimation and adjustment cycle required by prior art survey devices.

In addition to the equipment described above for accurately computing a current position, the survey system may include a handheld device 200, a range pole 210, an orientation device 270, and a pointing device 280. The handheld device 200 includes appropriate circuitry and software to process positioning information from the global positioning system (GPS), or similar system, as well as to process correction signals to adjust the positioning information received to determine a corrected, more accurate current position. Additionally, the handheld device 200 includes circuitry and software for controlling and commanding the orientation device 270 and the pointing device 280. For example, according to one embodiment of the present invention, upon determining the desired location 250 is within a predetermined distance of the current location, the pointing device may be activated causing it to illuminate the desired location 250 with a highly visible laser beam 290. In alternative embodiments, the handheld device 200 is an integrated controller that is mounted to the range pole 210 rather than being carried separately.

Figure 2:
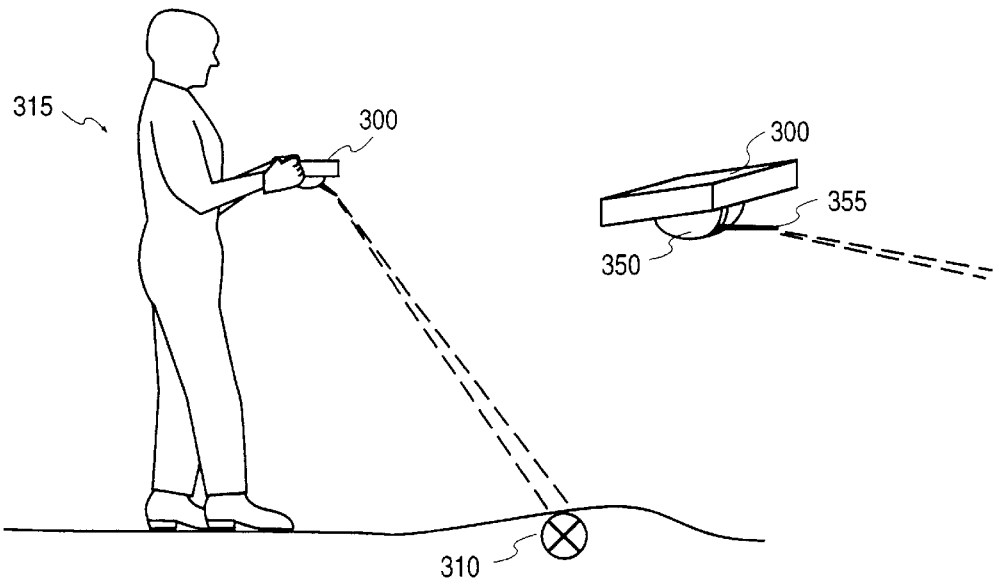
FIG. 2 is a simplified illustration of an embodiment of a handheld surveying device of the present invention.
Figure 3:
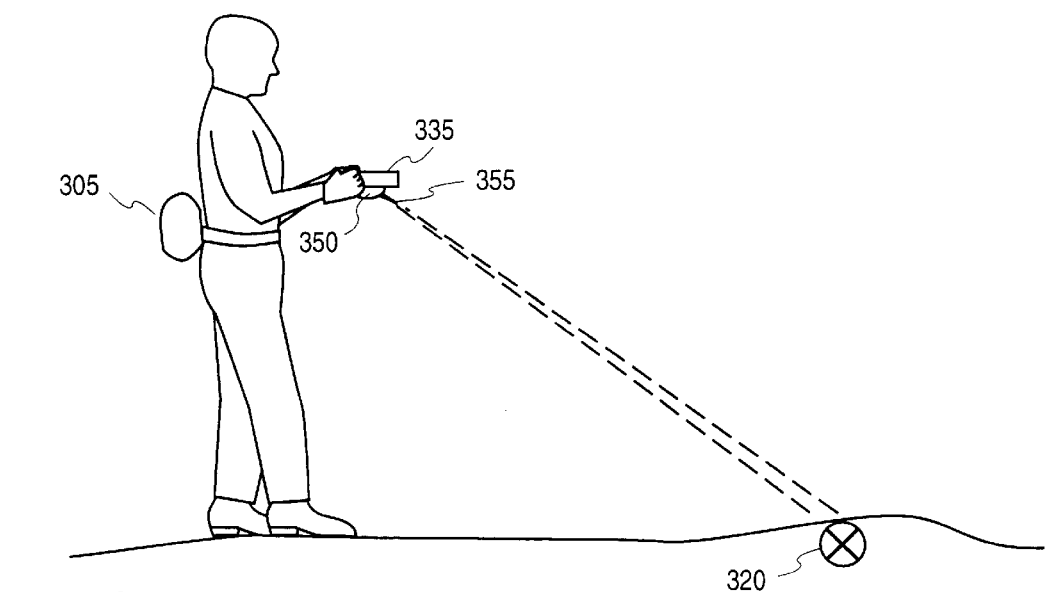
FIG. 3 is simplified illustration of an alternative embodiment of a handheld surveying device of the present invention.

Alternative embodiments are illustrated in FIG. 2 and FIG. 3. In these embodiments, the orientation device 350 and the pointing device 355 are mounted to the housing of a handheld survey device 335 and the range pole 210 may be eliminated.

In the embodiment depicted in FIG. 3, certain components are placed in a fanny pack 305 which hooks around the user's waist with a belt. For example, the equipment for maintaining the wireless link, such as radio modem 170 and the data storage device may be placed in the fanny pack 305, freeing up space in the handheld portion 335 of the device. However, it is preferred that the pointing device 355, the orientation device 350, GPS antenna and digital level and heading device be maintained in the handheld portion 335 of the device to allow accurate position data to be measured and facilitate position identification by the pointing device 335.

Figure 4A:
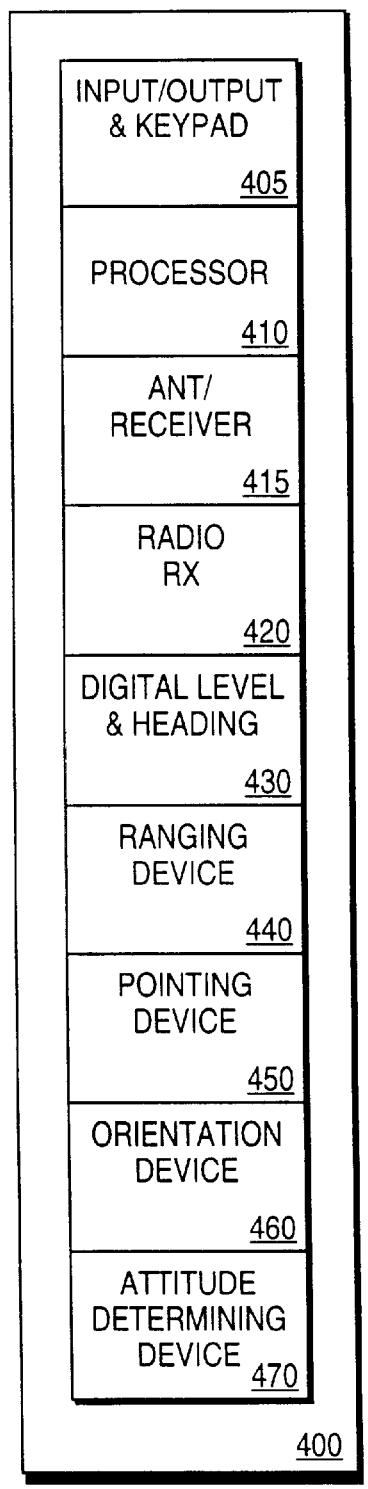
FIG. 4A is a simplified block diagram illustrating various functional units according to one embodiment of the surveying system of the present invention.

Exemplary functional units that may be included in various embodiments and distributed among the control unit mounted to the range pole 210, the handheld device 200, and the backpack 160 or fanny pack 305 (collectively referred to as the survey system) will now be described with reference to the simplified block diagram of FIG. 4A. It should be appreciated all the functional units will be distributed between the fanny pack 305 and the handheld device (300 or 335) according to the embodiments depicted in FIG. 2 and FIG. 3. In any event, the survey system 400 typically includes input/output elements, such as a display and keypad 405, a processor 410, and related components such as memory, controllers and the like, a positioning antenna and receiver 415, a radio receiver 420, a digital level and heading element 430, a pointing device 450, an orientation device 460, and an attitude determining device 470.

The input/output display and keypad 405 are used to provide feedback to the user and enable the user to enter in information, such as notes regarding the survey process performed. Processor 410 performs the computations necessary to determine the distance and direction of the desired position, and further controls the remaining elements to acquire the data needed to perform these calculations. Processor 410 also performs functions such as storing data in the memory for subsequent access, and displaying selective information on the display during survey, such as an indication of the distance and direction of the desired position relative to the user's current position.

The antenna and receiver 415 receive position information with respect to the location of the antenna of the device. In the present embodiment, equipment compatible with the Global Positioning System (GPS) are employed. However, it is readily apparent an antenna and receiver compatible with other types of positioning systems may be employed. Other types of positioning systems include the Global Orbiting Navigation System (GLONASS), long-range navigation (LORAN-C) system, uncoordinated beacon signals, and pseudolite systems.

In an alternative embodiment, the survey system 400 includes a receiver compatible with an inertial navigation system (INS) that is used to determine position information based on a known reference position. In one embodiment, the INS system uses gyroscopes to sense attitude changes and integrating accelerometers to measure acceleration components of the moving system. The receiver receives the information from the gyroscopes and accelerometers to determine the current position of survey system 400 based on the reference position that may, for example, be input by the user of the system. INS systems are well known to those skilled in the art and are described in "Understanding the Navstar: GPS, GIS, and IVHS" by Tom Logsdon.

In another embodiment, survey system 400 includes an integrated navigation system that combines an INS with the external positioning systems discussed above, for example, GPS. Because an INS requires a known reference position, inertial navigation is a dead reckoning technique that results in drift errors with the passage of time. By using an external navigation system in combination with the INS, the reference position can be updated periodically, resulting in improve accuracy in survey system 1020. The INS may also be used in combination with GPS to provide positioning information when satellite information is unavailable due to, for example, satellite malfunctions, receiver malfunctions, terrestrial blockages, or signal jamming. In another embodiment, an INS is used to assist a GPS by providing accurate initial estimates on position and velocity, thus reducing the time required for the GPS receiver to lock onto signals streaming down from GPS satellites.

Once the position information is received, the difference in position between the device and the desired position may be determined. For example, in one embodiment, the digital level and heading device 430 identifies the tilt (also referred to as pitch) and the heading (also referred to as yaw) at which the device is oriented. This provides data that may be used to determine the relative position and orientation of the device with respect to the desired position. Thus, in embodiments incorporating the digital level and heading device 430, there is no need for the user to hold the handheld device in a specific orientation. The device 430 may be embodied as two separate devices, one determining the level of the handheld device, and the other determining the heading, for example. Alternately, the device 430 may be one integrated device. One example of such a device is the TMCI which is available from Precision Navigation Ltd., Sunnyvale, Calif.

In alternative embodiments of the present invention, the system 400 may also include an attitude determining device 470 for determining the angular orientation of the device, such as a flux gate compass or TANS vector system.

Referring now to the pointing device 450, this device provides an indication to the user of the location of the desired position. In one embodiment, a laser pointer is used. The laser pointer illuminates a spot on a surface of the ground corresponding to the location of the desired position input by the user. An exemplary laser module that may serve as the pointing device 350 is the MLX-635 manufactured by RPMC of St. Charles, Mo.

According to one embodiment, the pointing device 450 is mounted to the orientation device 460. The orientation device 460 is oriented based upon parameters, such as an indication of the desired bearing and elevation, received from the processor 410. In this manner, the orientation device 460 provides a mechanism by which the pointing device 450 may be aligned with the desired position. In one embodiment, the orientation device 460 may provide freedom of movement about a first and a second axis. For instance, the orientation device 460 may be similar to a miniature turret, which rotates about a base to the appropriate heading and raises or lowers the pointing device 450 to the appropriate angle relative to the horizontal.

In an alternative embodiment, the pointing device 450 may remain in a fixed position and the orientation device 460 is a deflection mechanism such as a piezo-electrically controlled mirror. In this manner, the pointing device 450 may remain stationary and the orientation device 460 aligns the laser beam with the desired position by appropriately adjusting the angle of the deflection mechanism. In this embodiment, for the largest degree of freedom for controlling the direction of the laser beam, the pointing device 450 is preferably fixed in a vertical position perpendicular to the measurement platform (e.g., the handheld device).

Importantly, while the pointing device 450 and the orientation device 460 are depicted as separate functional units, they need not be physically separate components. Rather, the orientation device 460 may be integrated within the pointing device 450 to control the laser beam internal to the pointing device 450. Additionally, the orientation device 460 need not be a mechanical mechanism. Those of ordinary skill in the art will appreciate various other means for orienting the pointing device 450, are available.

For example, in one embodiment, the pointing device 450 may comprise one or more optical fibers that are positioned by manipulating an electrostatic field though which the one or more optical fibers pass.

In alternative embodiments, a ranging device 440 may also be included to provide the user with feedback and allow for correction of a two dimensional position that may be located on a rising slope, for example. The ranging device 440 may be used to measure the distance between the device and the indicated location of the desired position. Preferably, the measuring element 440 is any compact measuring device that functions to non-obtrusively measure the distance between the device and the location indicated by pointing device 450. In addition, it is preferable that the ranging device 440 not require an additional device, such as a reflective object, to be placed at the indicated location. One example of such a measuring device 440 is a sonic-based measuring system, which sonically determines the distance between the measuring device 440 and another location. Another device 440 that can be used is a laser-based measuring device that uses the time of flight or performs a phase comparison in order to measure the distance. Examples of measuring element products include Criterion by Laser Technology Colorado, and Pulsar by IBEO, Hamburg, Germany.

Preferably, the system 400 is also capable of performing one or more correction techniques for improving the position fix accuracy. For example, the system 400 may include a radio receiver 420 for receiving additional data, such as RTK data, differential GPS correction signals, or other data for increasing the accuracy of the measurements. Correction signals may be transmitted by a DGPS base station, for example, and received by the radio receiver 420. These correction signals are then used to adjust the positioning data received through the GPS antenna and receiver 415. Although in the present embodiment, a separate antenna/receiver is used, it is contemplated that one antenna/receiver can be used to receive position signals and correction signals. In one embodiment, the radio receiver 420 may comprise a Trim Talk 900 radio modem manufactured by Trimble Navigation Limited. Importantly, however, the radio receiver 420 may be any device capable of supporting a wireless link with the base station, such as a wireless or cellular modem, a radio receiver or other RF capable device. Further, when direct radio communication between the reference station and the rover device may be obscured, the radio receiver 420 may be configured to operate with one or more repeaters. Additionally, it should be appreciated that additional elements may be added to the system to provide additional functionality and application-specific features as may be required for various applications.

Figure 4B:
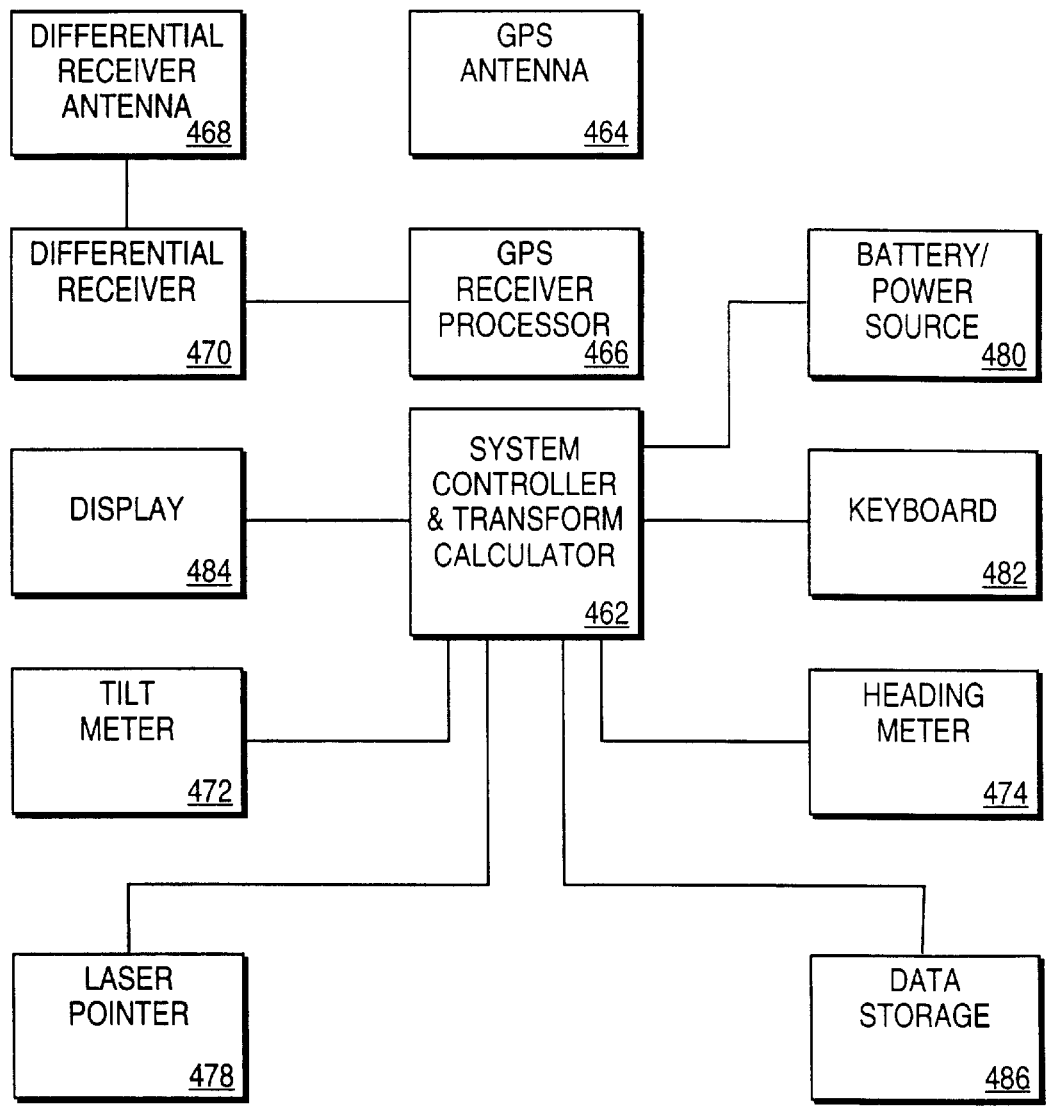
FIG. 4B illustrates an alternate embodiment of the surveying system of the present invention.

FIG. 4B is a simplified block diagram of an alternate embodiment of the system of the present invention. The device 460 is controlled by system controller and transform calculator 462. Positioning signals are received via a GPS antenna 464 and input to GPS Receiver/Processor 466. Then, the GPS Receiver/Processor may perform differential correction using data received via a differential receiver antenna 468 and receiver 470. As is readily apparent to one skilled in the art, however, other forms of correction may be employed. One such method is known in the art as the RTK method in which a reference GPS station positioned at a known location receives well known GPS observables and makes them available via a radio link, for example, in real-time to the rover device. The rover device may then processes those observables as well as its own observables to determine a more accurate position fix relative to the reference station. The method is described in U.S. Pat. No. 5,519,620 of Talbot et al., which is incorporated herein by reference.

In any event, positioning data is transferred to the system controller and transform calculator 462 by GPS receiver processor 466. Transforms, examples of which are described below, are applied to the positioning data received based upon the pitch, roll, yaw, and bearing of the device as indicated by various meters such as the tilt meter 472 (e.g., one or more inclinometers), heading meter 474, and others described previously. The resulting parameters may be used to orient the laser pointer 478 so that it will illuminate the location of the desired position when the laser is activated.

The system 460 also may include a battery or other power source 480 used to power the device 460, a keyboard 482 to enable the user to input data such as notes or the like, and a display 484 to provide the usual feedback to the user. Data storage 486 is also included for temporary and semi-permanent storage of data collected and computed in accordance with the teachings of the present invention.

Figure 5:
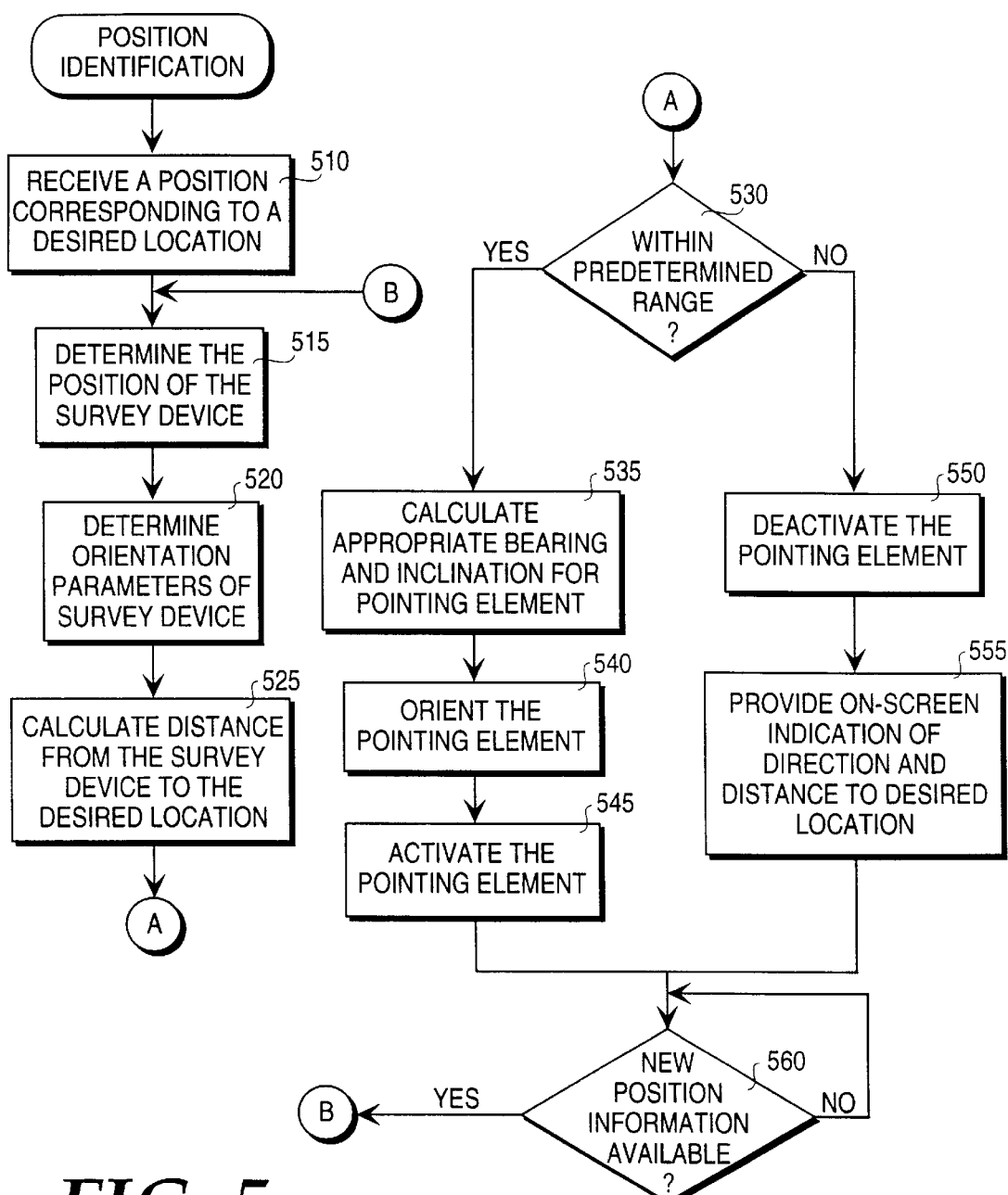
FIG. 5 is a simplified flow diagram illustrating the position identification processing according to one embodiment of the present invention.

An exemplary process for performing position identification will now be described with reference to FIG. 5. Initially, a position is received from the user, for example, representing the desired position that is to be located. At step 515, the current position of the survey device is determined based upon position information received from positioning system signals and additionally based upon correction signals, if available. At step 520, the orientation parameters of the survey device are determined. At step 525, the distance from the survey device to the desired position is calculated using the current position determined in step 515. According to the embodiment depicted, at step 530, a comparison is performed to determine if the distance from the desired location is within a predefined range. Preferably, the predefined range is less than or equal to the range of the laser diode used in the pointing device. At any rate, if the condition is satisfied, then processing continues with step 535; otherwise processing continues with step 550. At step 535, parameters for aligning the pointing element with the desired position are calculated. For example, the appropriate bearing and angle of elevation to bring the pointing element in alignment with the desired position are determined. At step 540, the parameters calculated at step 535 are used to orient the pointing element. Finally, at step 545, the pointing element is activated so as to illuminate the location corresponding to the desired position. If the survey device was determined not to be within the predetermined range at step 530, then at step 550, the pointing element may be deactivated. At step 555, an on-screen indication of the direction and distance relative to the user's current heading and position may be provided to the user. In alternative embodiments, rather than deactivating the pointing element and providing an on-screen indication of the distance and direction to the desired position, the pointing device may be configured to provide the indication. For example, the pointing device may sweep or point in the appropriate direction. At step 560, a determination is made as to whether new position information has become available. If so, the process may be repeated starting with step 515. In this manner, while the user remains within the predetermined range, the pointing device will track the location of the desired position. In should be appreciated in alternative embodiments the pointing device may be manually activated/deactivated rather than being activated and deactivated based on the distance to the desired position.

Thus, a user can easily navigate to and locate a desired position without performing the iterative estimation and confirmation cycle required with survey devices of the prior art.

FIG. 6A illustrates a bottom view of the handheld surveying device 300 according to one embodiment of the present invention. The pointing device 355 is shown before and after the orientation device 350 has been rotated θ degrees in azimuth. FIG. 6B illustrates a side view of the handheld surveying device 300 according to one embodiment of the present invention. The pointing device 355 is shown before and after the orientation device 350 has rotated it −Ø degrees in elevation.

Figure 6C:
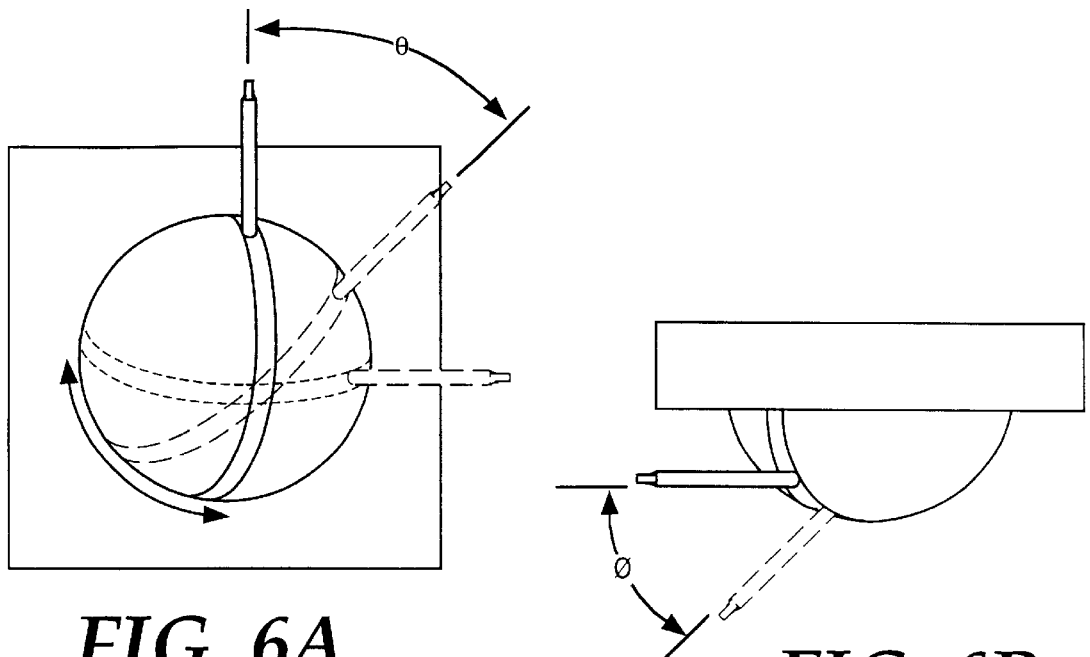
FIG. 6C is a diagram used to describe exemplary computations that may be performed according to one embodiment of the present invention.
Figure 6C:
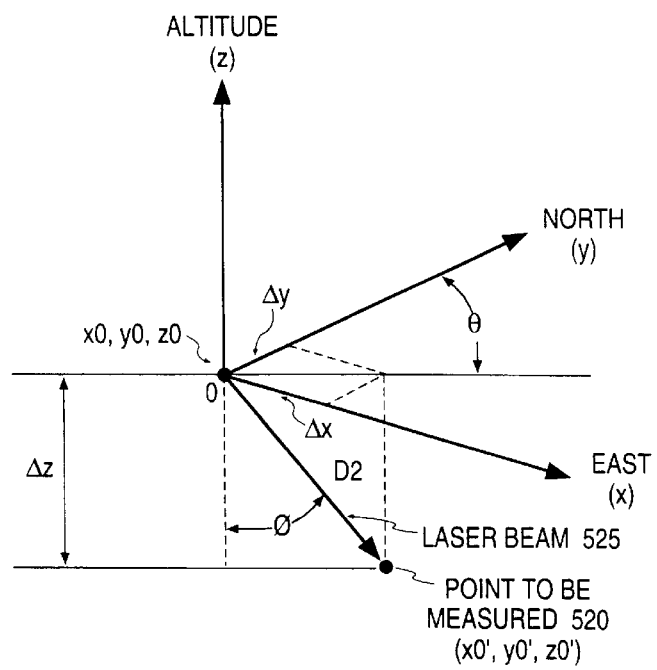

Having illustrated how the pointing device may be positioned, exemplary bearing and elevation calculations to be performed by the survey device of the present invention will now be described with respect to FIG. 6C. To orient the pointing device at a known position given in latitude and longitude (or any x,y,z coordinate system) such that it is in alignment with the coordinates of a predetermined position, the following coordinate transform is used. For purposes of explanation, a local coordinate system in x, y, z as shown in FIG. 6C is defined, where x corresponds to East, y corresponds to North, and altitude corresponds to z. The origin is centered on the source of the laser beam. The coordinates of the origin are referred to by $x_o$, $y_o$, $z_o$. The coordinates of the point 620 to be identified are called $x_o'$, $y_o'$, $z_o'$. Let Ø be the elevation of the laser beam in degrees from horizontal. Let θ be the angle of the laser beam projected on the local horizontal plane (x, y) representing the bearing from survey device azimuth. Angles Ø and θ may be determined as follows relative to true north and relative to a level measurement platform:

$$\theta = \mathrm{ArcTan}\left(\frac{x_0' - x_0}{y_0' - y_0}\right)$$

$$\text{Ø} = \mathrm{ArcTan}(\sqrt{((x_0'-x_0)^2+(y_0'-y_0)^2)}/(z_0'-Z_0))$$

Figure 7:
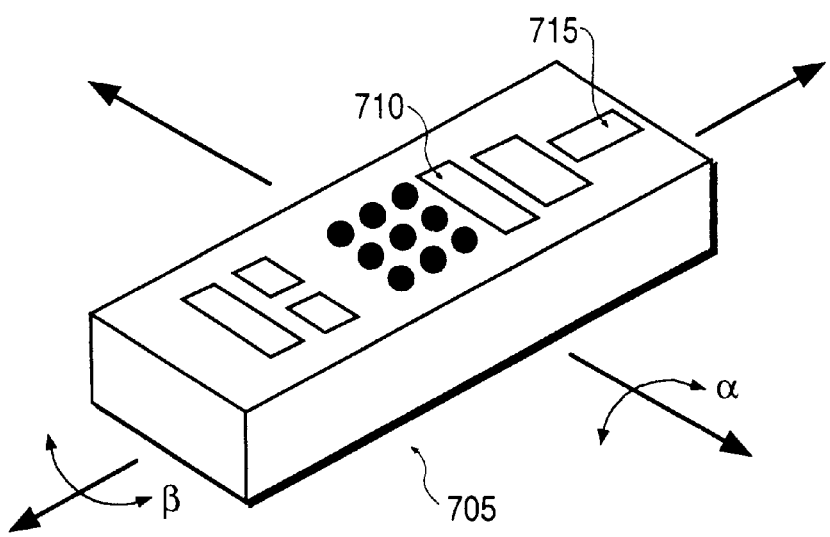
FIG. 7 is a diagram used to describe exemplary computations that may be performed in another embodiment of the present invention.

Ultimately, the attitude of the survey device should be delivered to a right and regular orientation either by holding the device true north and level in two horizontal planes or, as is well known in the art, the calculations above may be modified to incorporate the orientation of the platform by using the attitude of the survey device (the measurement platform) such as may be determined by two inclinometers mounted at right angles to each other as shown in FIG. 7. Such inclinometers may have electronic readout means coupled to the system controller and transform calculator 462 thereby allowing offsets from the two horizontal planes to be automatically taken into consideration by the system controller and transform calculator 462.

As illustrated in FIG. 7, the handheld device 705 may include two inclinometers, such as bubble inclinometers 710 and 715, oriented perpendicular to one another. While in the embodiment depicted the two inclinometers 710, 715 are located in the same elevation plane, it is appreciated in alternative embodiments they may be located at any elevation ($\Delta z$) independently of one another. The first inclinometer 710 measures the tilt of the device along the lengthwise axis (angle $\alpha$) in the yz plane which corresponds to "pitch." The second inclinometer 715 measures the tilt along the width-wise axis (angle $\beta$) in the xz plane which corresponds to "roll." If the survey device 705 is to be handheld, then the inclinometer measurements (e.g., $\alpha$ and $\beta$) and the survey device's orientation as measured by the appropriate device may be used in conjunction with an additional coordinate transformation to account for the attitude of the survey device 705. Mechanisms for targeting and pointing to objects from a given platform and making measurements on that platform to determine what the coordinates are of the distant point are well known and are discussed in detail in U.S. Pat. No. 5,568,152 of Janky et al. entitled "Integrated Image Transfer for Remote Target Location" and U.S. Pat. No. 5,644,318 of Janky et al. entitled "SATPS Dynamic Surveying from a Moving Platform" the contents of which are hereby incorporated by reference.

Figure 8:
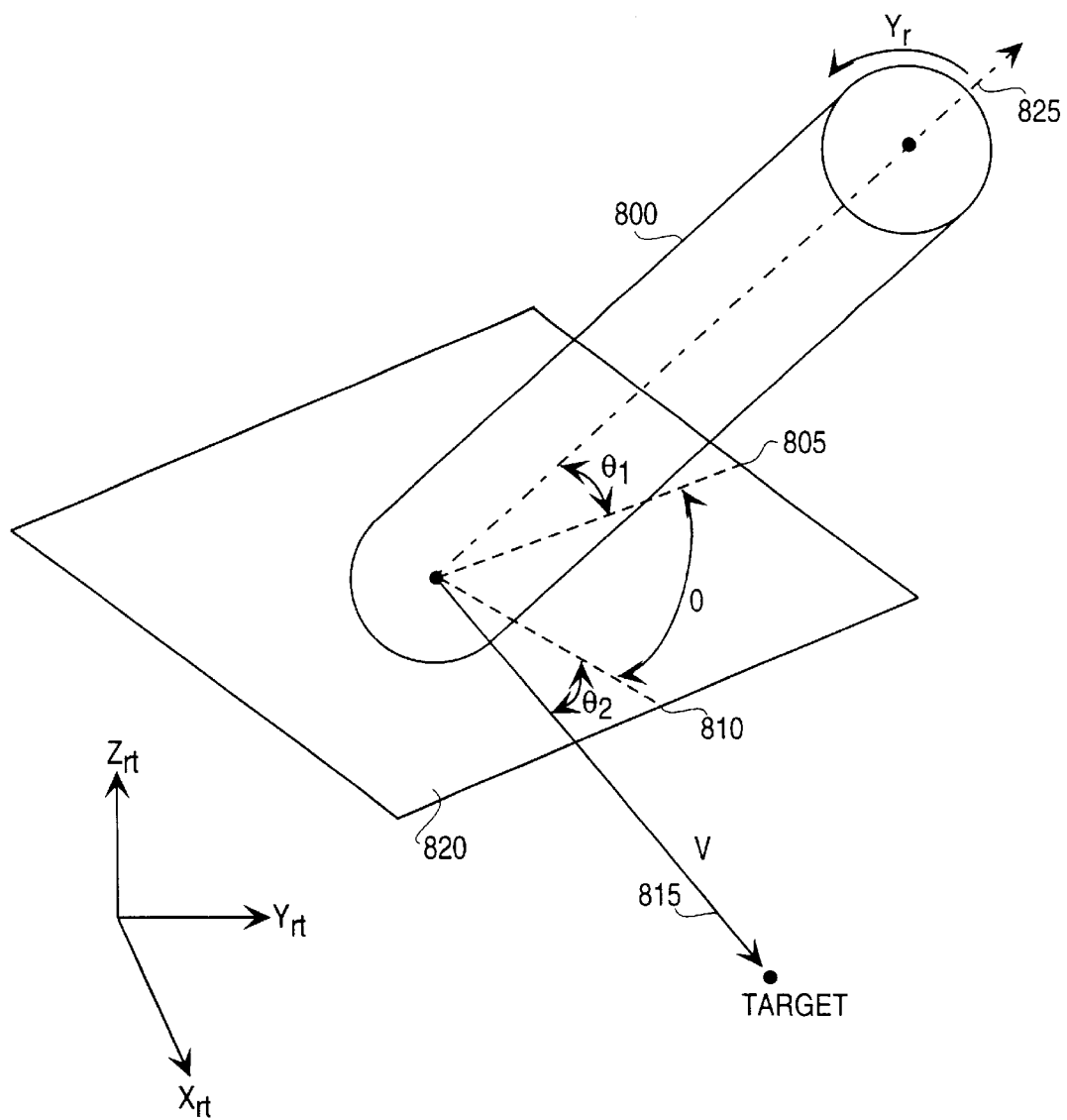
FIG. 8 illustrates an exemplary transformation from a receiver coordinate system to a neutral coordinate system.

FIG. 8 is useful for describing an exemplary matrix transformation from a receiver coordinate system $(x_r, y_r, z_r)$ to a neutral coordinate system $(x_{rt}, y_{rt}, z_{rt})$ to account for the attitude of the receiver 800. A receiver axis 825 is projected onto a horizontal plane 820 to produce a projected receiver axis 805. A receiver-target separation vector, v, is projected onto the horizontal plane 820 to produce a projection of the receiver-target separation vector 810. The exemplary matrix transformation is then as follows:

$$\begin{bmatrix} x_n \\ y_n \\ z_n \end{bmatrix} = \begin{bmatrix} \cos(\theta_1 + \theta_2) & 0 & -\sin(\theta_1 + \theta_2) \\ 0 & 1 & 0 \\ \sin(\theta_1 + \theta_2) & 0 & \cos(\theta_1 + \theta_2) \end{bmatrix} \begin{bmatrix} \cos\phi & -\sin\phi & 0 \\ \sin\phi & \cos\phi & 0 \\ 0 & 0 & 1 \end{bmatrix}$$

$$\begin{bmatrix} \cos\psi_r & 0 & -\sin\psi_r \\ 0 & 1 & 0 \\ \sin\psi_r & 0 & \cos\psi_r \end{bmatrix} \begin{bmatrix} x_r \\ y_r \\ z_r \end{bmatrix}$$

Figure 9:
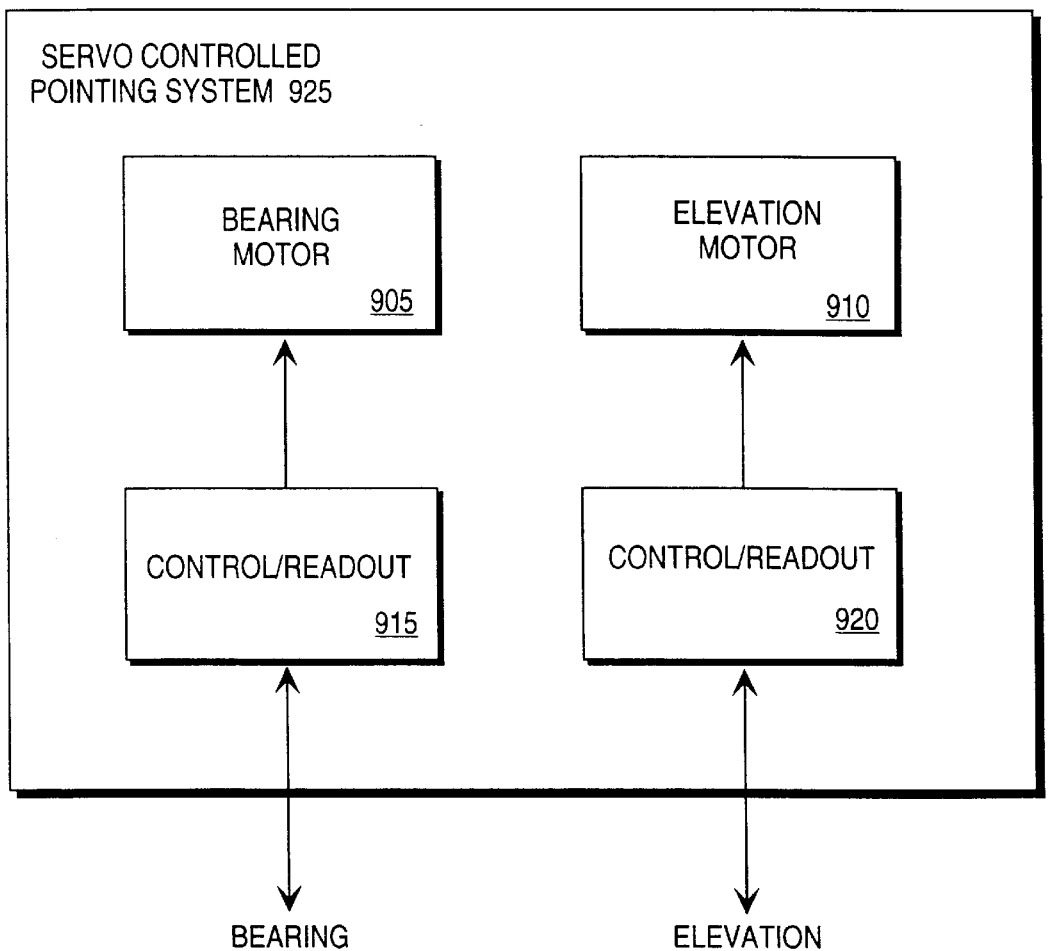
FIG. 9 is a simplified block diagram of an exemplary orientation device according to one embodiment of the present invention.

Referring now to FIG. 9, a simplified block diagram of an exemplary orientation device 900 will now be described. According to this embodiment, the orientation device 900 comprises a servo controlled pointing system 925. Such pointing systems are well known. For example, the techniques used to point the laser are similar to those used by radar or satellite antenna engineers to perform tracking of a distant object with servo control where the servo input here, however, is an arbitrary control signal (e.g., bearing and elevation values) rather than a signal from the source itself.

At any rate, according to the embodiment depicted, the servo controlled pointing system 925 includes a bearing motor 905 for rotating the pointing device about a first axis in azimuth and an elevation motor 910 for rotating the pointing device about a second axis in elevation. The bearing motor 905 is coupled to a control/readout device 915 which controls the bearing motor 905 based upon bearing commands. The elevation motor 905 is coupled to a control/readout device 915 which controls the elevation motor 910 based upon elevation commands. The control/readout devices 915, 920 each include a servo motor control system to allow independent control of the attached servo motor. The control/readout devices 915, 920 also provide an electronic means of reading out the current degree of rotation of servo motors 905, 910 (in azimuth and elevation, respectively). In this manner, the processor or system controller may monitor the progress of the pointing system.

Many alternative embodiments are contemplated in the present invention. For example, the invention may be in connection with locating buried objects. By way of illustration, rather than providing an indication of a fixed point, the survey device may be configured to sweep out the direction in which buried cables or utilities lie. Additionally, if the size of a buried object is known, the shape of the object may be drawn on the ground with the pointing device.

Further, the location of physical position marks may be located by incorporating the techniques disclosed in U.S. patent application Ser. Nos. 08/026,547 and 08/587,998, entitled "Location and Generation of High Accuracy Survey Control Marks Using Satellites" filed on Mar. 4, 1993, and Jan. 16, 1996, respectively, which are incorporated herein by reference. While the method and apparatus described herein may be used by surveyors looking for points of interest in their business of performing stake out, they may also be used by many other people for targeting activities to point to where things might be relative to a measurement platform.

As previously discussed in an above described embodiment, the pointing device of the survey system may be configured to provide indication of the distance and direction to the desired position. As noted in an above example, the pointing device may sweep or point in the appropriate direction to the desired position. In this manner, the pointing device may provide indication of a direction of travel to the desired position when the desired position is outside the range of the laser such that it would not be able to illuminate the spot on the ground corresponding to the exact location of the desired position. Thus, when outside the range, the illumination on the ground would provide indication of the direction of travel to the spot rather than indicating the exact spot of the desired position. In an alternative embodiment, the direction of travel may be indicated by other methods, for example, illuminating an arrow within a head mounted viewing device worn by the user. In one embodiment, the survey system may be mounted to a vehicle. For one embodiment, the digital level and heading device 430 of FIG. 4 may be incorporated into the survey system removing the need for the user to hold the handheld device in a specific orientation and allowing for operation of the system while mounted on a moving vehicle.

Figure 10:
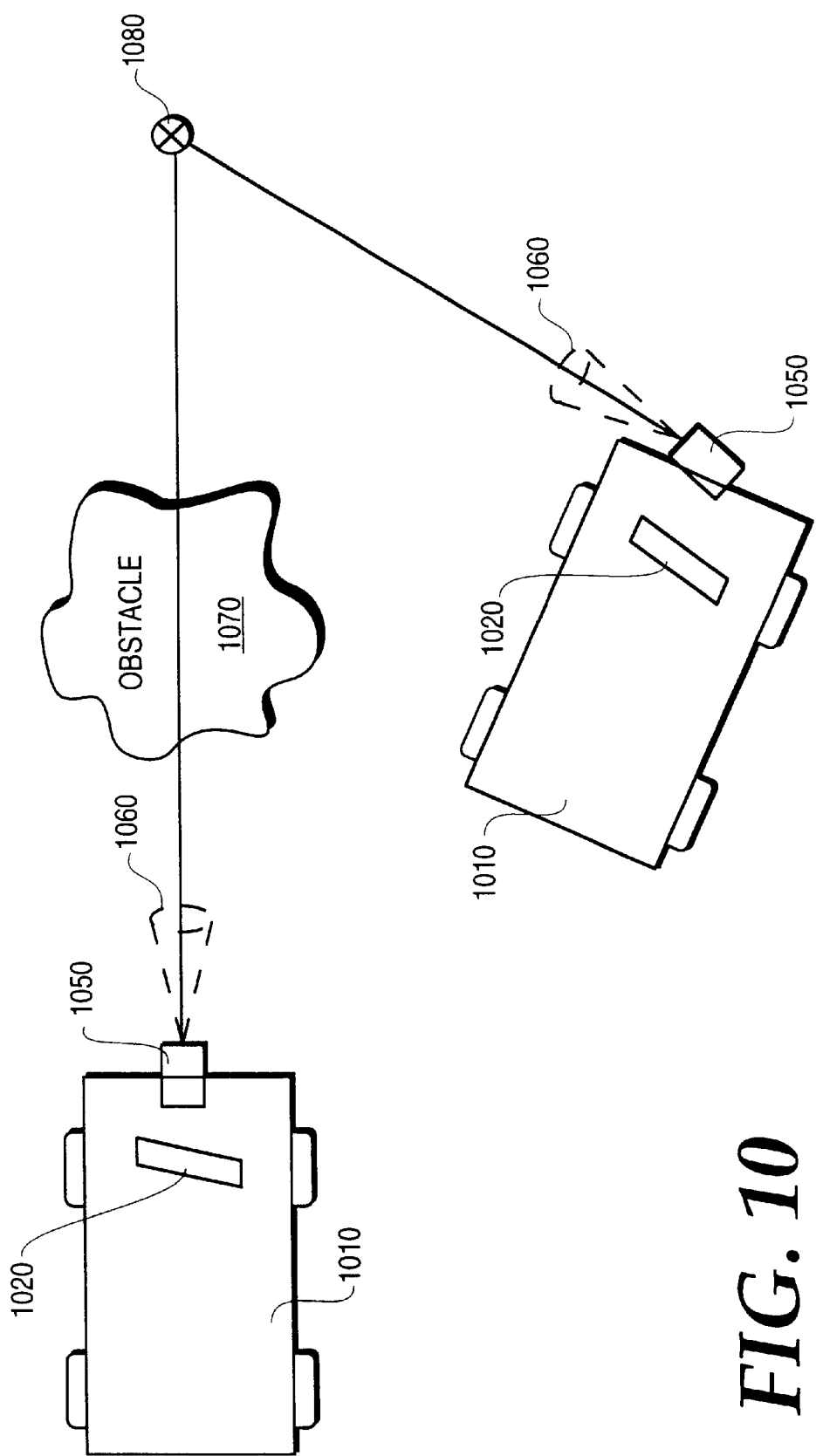
FIG. 10 illustrates an alternative embodiment where the survey system is mounted to a vehicle.

FIG. 10 illustrates one embodiment where the survey system is mounted to a vehicle (e.g., a truck) 1010. In one embodiment, the truck 1010 is a vibroseis truck used for land seismic surveying. Although the system is described with respect to a land vehicle, in alternative embodiments, the system may also be used with other types of vehicles, for examples, watercraft and aircraft. The survey system 1020 includes appropriate circuitry and software (e.g., digital level and heading device 430) to process positioning information received from the GPS, INS, or other systems discussed above, as well as to process corrections signal to adjust the positioning information received to determine a corrected, more accurate current position. The survey system also includes circuitry and software for controlling and commanding the orientation device and the pointing device as described above. In one embodiment, survey system 1020 is similar to the survey system 400 shown in FIG. 4A. In another embodiment, survey system 1020 is similar to the survey system shown in FIG. 4B.

Referring still to one embodiment illustrated in FIG. 10, the direction of travel to the desired position is identified by prominently illuminating a spot on the ground 1060 directly ahead of the truck 1010 using a pointing device 1050. In one embodiment, pointing device 1050 is a day visible laser, for example a green laser. Orientation device 350 of FIG. 3A may be used to position pointing device 1050 to illuminate a spot on the ground 1060 indicating the direction of travel to desired position 1080. Survey system 1020 maintains pointing device 1050 aligned with the desired position 1080 as vehicle 1010 changes its direction relative to the desired position in order to maneuver around an obstacle (e.g., a lake, trees, rocks) 1070. By displaying information in an area where the user will normally be looking to maintain safe driving, survey system 1020 eliminates the need for an operator of vehicle 1010 to divert his vision away from the safe steering of the vehicle in order to read the information on a navigation console.

While the pointing device is illustrated as a laser, it may also be other visible indicators, for examples: a mechanical arm, an illumination on the windshield of a vehicle, and an illumination on a head mounted viewing device. In one embodiment, the pointing device is a mechanical arm that is maintained in alignment with the desired position as the vehicle changes direction relative to the desired position. In another embodiment, the pointing device is implemented as a visible graphic on a heads-up display of the windshield of vehicle 1010 that is continuously adjusted to display the appropriate direction of travel as vehicle 1010 changes relative to the desired position.

Figure 11:
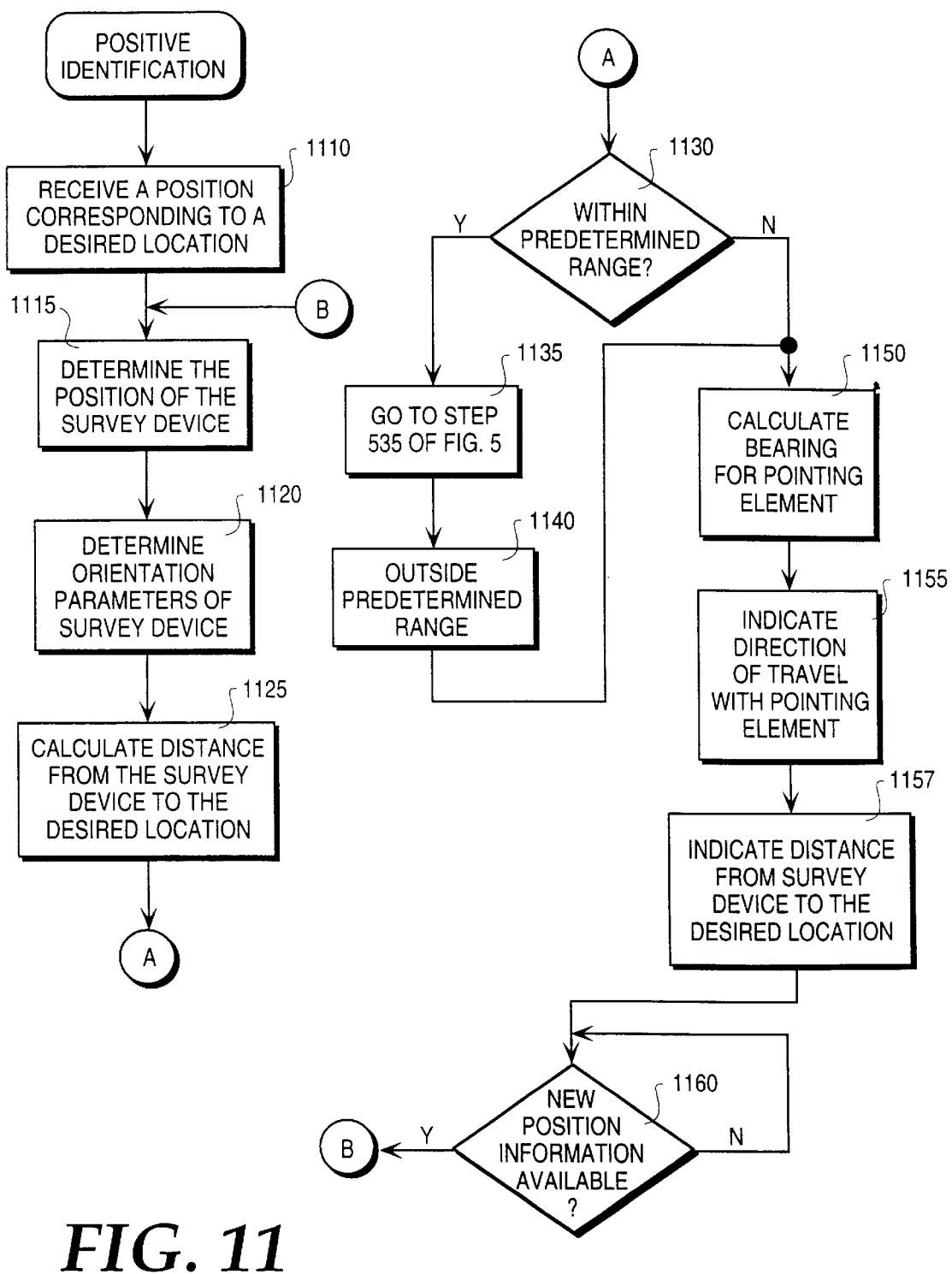
FIG. 11 illustrates the process for performing direction identification in accordance with one embodiment of the present invention.

FIG. 11 illustrates the process for performing direction identification in accordance with one embodiment of the present invention. Initially, a position is received from the user, for example, representing the desired position that is to be located, step 1110. At step 1115, the current position of the survey device is determined based upon position information received from positioning system signals and additionally based upon correction signals, if available. At step 1120, the orientation parameters of the survey device are determined. At step 1125, the distance from the survey device to the desired position is calculated using the current position determined in step 1115.

In accordance with the illustrated embodiment, at step 1130, a comparison may be performed to determine if the distance from the desired location is within a predefined range. In one embodiment, the predefined range is less than or equal to the range of the laser diode used in the pointing device 1050 of FIG. 10. If the condition is satisfied, then processing may continue with step 535 of FIG. 5, step 1135, until a time when the system is determined to once again be outside the predetermined range, step 1140, and the process continues with step 1150. If the survey device was determined not to be within the predetermined range then, at step 1150, the appropriate bearing to bring the pointing element in alignment with the desired position is determined. At step 1155, the parameters calculated at step 1150 are used to orient the pointing element so that it indicates the direction of travel to reach the desired position.

As discussed in one of the above described embodiments, the pointing device illuminates a spot on the ground to indicate the appropriate direction that the vehicle should be navigated to reach the desired position. The laser beam may be displayed differently when the survey device is outside or inside of the predetermined range. For example, the laser beam may be continuous when outside the range and modulated when the survey device is inside the predetermined range. In one embodiment, the laser beam is modulated at different frequencies based on the distance to the desired position. In addition, an indication that the user has reached the desired position may also be provided by the laser beam. In one embodiment, the pointing device illuminates a symbol on the ground (e.g., an arrow) that changes to a different symbol (e.g., a cross-hair) when the desired position has been reached.

In another embodiment, an audible signal may be used to indicate when the pointing device is within the range and, thus, illuminating the exact spot of the desired location. The audible signal may be continuous or may be intermittent with a frequency based on the distance to the desired position. Otherwise, no audible signal would be generated when the pointing device is outside the range, thereby indicating that only the direction of travel is being displayed.

At step 1157, an indication of the distance to the desired position relative to the user's current heading and position may be provided to the user. In one embodiment, an audible signal is used where the signal would begin at a low frequency and change towards a higher frequency as the vehicle approaches the desired location. In another embodiment, the processor in the survey system may audibly provide a read out of the distance information using a speaker wherein the user would hear the distance information. Using audio to provide distance information is an alternative, non-intrusive form of providing information to the user so as not to divert the users view from the vehicle's direction of travel.

At step 1160, a determination is made as to whether new position information has become available. New position information would become available if, for example, the vehicle changes its direction of travel relative to the desired position (e.g., to maneuver around an obstacle). If so, the process may be repeated starting with step 1115 so that pointing device 1050 of FIG. 10 is maintained in alignment with the desired position. In this manner, while the user is navigating the vehicle, the pointing device will track the location of the desired position.

The invention has been described in conjunction with the preferred embodiment. It is evident that numerous alternatives, modifications, variations and uses will be apparent to those skilled in the art in light of the foregoing description.

What is claimed is:

1. A method of identifying a direction to a desired position to a user of a survey device, the method comprising:

receiving a first position corresponding to the desired position;

determining a second position corresponding to a current position of the survey device; and orienting a pointing element to a first orientation, after the first position is determined, in which the pointing element is substantially aligned with the first and the second positions.

2. An apparatus for identifying a direction to a desired position to a user of a survey device comprising:

means for receiving a first position corresponding to the desired position;

means for determining a second position corresponding to a current position of the survey device; and means for orienting a pointing element to a first orientation, after the first position is determined, in which the pointing element is substantially aligned with the first and the second positions.

3. An apparatus for identifying a direction to a desired position to a user of a survey device comprising:

means for receiving a first position corresponding to the desired position;

means for determining a second position corresponding to a current position of the survey device;

means for orienting a pointing element to a first orientation in which the pointing element is substantially aligned with the first and the second positions;

means for determining a third position corresponding to a-new position of the survey device; and means for orienting the pointing element to a second orientation in which the pointing element is substantially aligned with the first and the third positions.

4. The apparatus of claim 3, further comprising:

means for determining the distance between the first position and the third position; and means for providing indication of the distance to the desired location.

5. The apparatus of claim 3, further comprising means for identifying the desired position with the pointing element if the distance is within a predetermined range.

* * * * *